(12) United States Patent
Shimoe et al.

(10) Patent No.: US 6,746,433 B1
(45) Date of Patent: Jun. 8, 2004

(54) DISPOSABLE PULL-ON GARMENT

(75) Inventors: Nariaki Shimoe, Kagawa-ken (JP); Yoshinori Kumasaka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/630,693

(22) Filed: Aug. 2, 2000

(30) Foreign Application Priority Data

Aug. 3, 1999 (JP) ............................................. 11-220424
Oct. 4, 1999 (JP) ............................................. 11-283192

(51) Int. Cl.⁷ ........................... A61F 13/15; A61F 13/20
(52) U.S. Cl. .................................. 604/385.01; 604/369
(58) Field of Search ................................. 604/365, 366, 604/369, 379, 380, 385.01, 385.22, 386–387, 385.24–385.31, 393–396, 391

(56) References Cited

U.S. PATENT DOCUMENTS

| | | | | |
|---|---|---|---|---|
| 2,695,615 A | * | 11/1954 | Del Guercio | 604/394 |
| 4,850,991 A | * | 7/1989 | Nakanishi | 604/391 |
| 4,887,602 A | * | 12/1989 | O'Leary | 604/385.25 |
| 4,916,005 A | * | 4/1990 | Lippert et al. | 428/192 |
| 4,940,464 A | * | 7/1990 | Van Gompel et al. | 604/396 |
| 5,531,729 A | * | 7/1996 | Coles et al. | 604/385.29 |
| 5,545,158 A | * | 8/1996 | Jessup | 604/385.3 |
| 5,685,874 A | * | 11/1997 | Buell et al. | 604/396 |
| 5,782,819 A | | 7/1998 | Tanzer et al. | |
| 5,858,013 A | | 1/1999 | Kling | |
| 5,868,725 A | * | 2/1999 | Coles et al. | 604/385.23 |
| 5,904,675 A | * | 5/1999 | Laux et al. | |
| 5,957,878 A | * | 9/1999 | Gilliam | |
| 6,083,212 A | * | 7/2000 | Kumasaka | 604/385.29 |
| 6,135,988 A | * | 10/2000 | Turner et al. | 604/387 |
| 6,174,303 B1 | * | 1/2001 | Suprise et al. | 604/391 |
| 6,210,386 B1 | * | 4/2001 | Inoue | 604/385.13 |
| 6,258,076 B1 | * | 7/2001 | Glaug et al. | 604/387 |
| 6,277,106 B1 | * | 8/2001 | Boudry et al. | 604/386 |
| 6,383,431 B1 | * | 5/2002 | Dobrin et al. | 264/154 |
| 6,454,747 B1 | * | 9/2002 | Shimada et al. | 604/312 |
| 6,478,784 B1 | * | 11/2002 | Johnson et al. | 604/385.01 |
| 2001/0049512 A1 | * | 12/2001 | Kawamura et al. | 604/312 |
| 2002/0174934 A1 | * | 11/2002 | Johnson et al. | 156/83 |

FOREIGN PATENT DOCUMENTS

| | | | |
|---|---|---|---|
| EP | 0873739 | * | 10/1998 |
| JP | 5-272066 | * | 10/1993 |
| JP | 11-104180 | | 4/1999 |
| WO | 9522306 | * | 8/1995 |
| WO | 0069384 | * | 11/2000 |

* cited by examiner

Primary Examiner—Karin Reichle
(74) Attorney, Agent, or Firm—Clark & Brody

(57) ABSTRACT

A disposable pull-on garment has an elasticized waist-opening and a pair of elasticized leg-openings. At least one of the inner or outer surfaces of a peripheral edge of the waist opening includes a slippage resistant sheet. The sheet has a high friction coefficient so that the peripheral edge of the waist opening is easily and reliably gripped when the garment is pulled on by a wearer.

9 Claims, 4 Drawing Sheets

DISPOSABLE PULL-ON GARMENT

BACKGROUND OF THE INVENTION

This invention relates to a disposable pants-type garment.

In the disposable pull-on garment such as a disposable pull-on diaper, a sheet, for example, of a nonwoven fabric having a relatively low friction has conventionally been used as a topsheet so that the wearer's skin may experience a comfortable touch. Japanese Patent Application Disclosure No. 1999-104180 describes a pull-on diaper provided on the outer surface of its backsheet with a plurality of window-like recesses adapted to be engaged with the finger tips as the diaper is pulled upward along the wearer's torso with a peripheral edge of a waist-opening held with the finger tips after the wearer's legs have been put through the diaper. The window-like recesses function to prevent the finger tips from slipping off from the peripheral edge of the waist-opening.

In the case of such a pull-on diaper of prior art, it is considerably difficult or troublesome for both the baby and the aged to localize the window-like recesses and then to insert his or her finger tips into them if the diaper must be put on his or her body by his or her own hands.

SUMMARY OF THE INVENTION

It is an object of this invention to provide a disposable pull-on garment improved so that the peripheral edge of the waist-opening may be easily and reliably held with the wearer's own finger tips.

There is provided a disposable pull-on garment having an elasticized waist-opening and a pair of elasticized leg-openings. The garment further comprises a front waist region, a rear waist region, and a crotch region. The front and rear regions are joined along transversely opposite side edges thereof to form a the waist-opening and a the pair of leg-openings. Respective peripheral edges of the waist-opening and a pair of leg-openings are elastic. Each of the front and rear regions have inner and outer surfaces which include inner and outer peripheral edge surfaces of the waist opening and inner and outer surfaces of remaining zones. At least one of the inner and outer peripheral edge surfaces of the waist-opening is provided with a slippage-resistant sheet having a friction coefficient higher than a friction coefficient of the inner surfaces of the remaining zones.

DETAILED DESCRIPTION OF THE PREFERRED EMBODIMENTS

Details of this invention will be more fully understood from the description of a disposable pull-on diaper as one embodiment as will be given hereunder with reference to the accompanying drawings.

Figure 1:
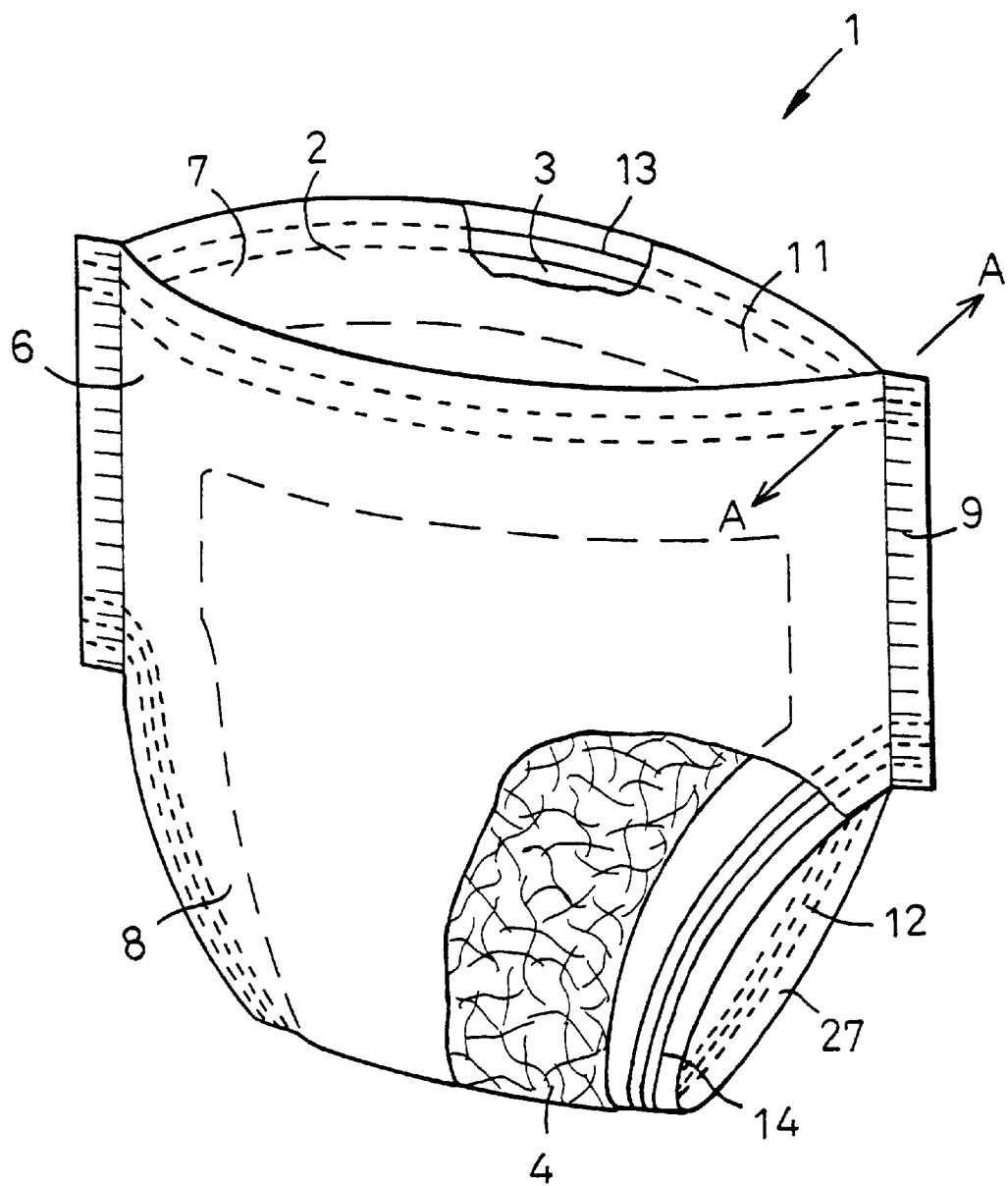
FIG. 1 is a perspective view showing a partially cutaway disposable pull-on diaper exploited in accordance with this invention as partially broken away.

A pull-on diaper 1 shown by FIG. 1 in a perspective view partially broken away comprises a liquid-pervious topsheet 2, a liquid-impervious backsheet 3 and an absorbent core 4 disposed between these two sheets 2, 3. Configurationally, the diaper 1 is composed of a front waist region 6, a rear waist region 7 and a crotch region 8 extending between these two waist regions 6, 7. The front and rear waist regions 6, 7 respectively have their transversely opposite side edges put flat and joined together at spots 9 arranged intermittently along the respective side edges in vertical direction to form a waist-opening 11 and a pair of leg-openings 12. Portions of the topsheet 2 and the backsheet 3 extending outward beyond a peripheral edge of the absorbent core 4 are joined to each other. In the vicinity of the waist-opening 11 and the leg-openings 12, elastic members 13 associated with the waist-opening 11 and elastic members 14 associated with the leg-openings 12 circumferentially extend between the topsheet 2 and the backsheet 3 and are secured under tension to the inner surface of at least one of these sheets 2, 3.

Figure 2:
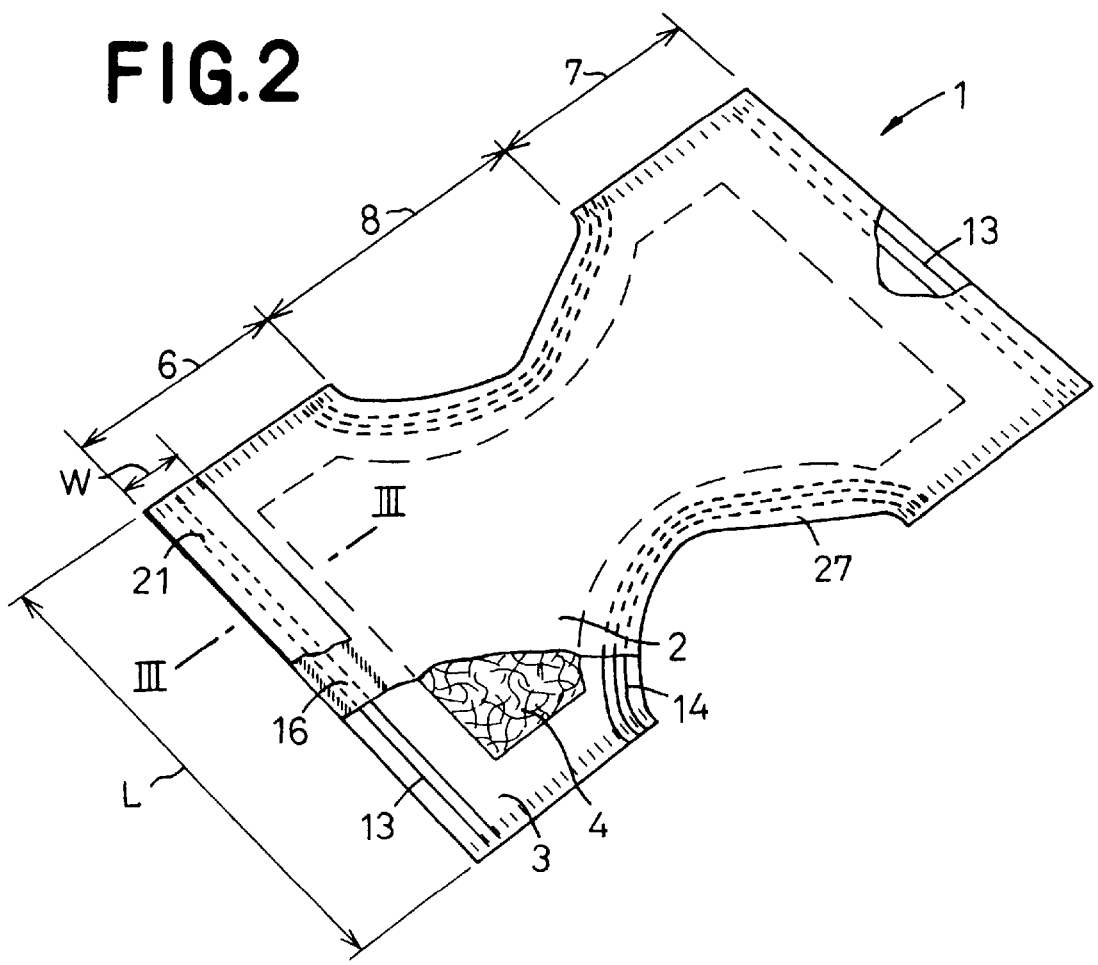
FIG. 2 is a perspective view showing the partially cutaway diaper in its developed state.

FIG. 2 is a perspective view partially broken away, showing the diaper 1 of FIG. 1 as the front and rear waist regions 6, 7 are separated from each other along the respective arrays of the spots 9 and developed in a direction indicated by a double-headed arrow A—A. Along an upper end 16 of the front waist region 6 which defines the waist-opening 11, a slippage-resistant sheet 21 having its surface of a relatively high friction coefficient is attached on the upper surface of the topsheet 2. This slippage-resistant sheet 21 has a width W as measured longitudinally of the diaper 1 (i.e., vertically of FIG. 1) and a length L as measured circumferentially of the trunk regions. The slippage-resistant sheet 21 has a friction coefficient higher than that of the topsheet 2 and more specifically has a static friction coefficient of 0.8 or higher and a dynamic friction coefficient of 0.035 or higher both measured by a measuring apparatus KES-G5 of KATO TECH Co., Ltd. (Kyoto City, Kyoto Prefecture, Japan). The width W of the slippage-resistant sheet 21 extends downward from the waist-opening's peripheral edge of the diaper 1 preferably beyond the elastic member 13 associated with the waist-opening 11. An upper limit of the width W is 60 mm. The length L is at least 20 mm and preferably extends over an entire width of the front waist region 6 as shown. It is undesirable to form the upper end 16 of the disposable diaper 1 only by the slippage-resistant sheet 21 since this would complicate making the diaper. The slippage-resistant sheet 21 as illustrated may be replaced by a plurality of relatively short slippage-resistant sheets 21 arranged intermittently in the circumferential direction.

Figure 3:
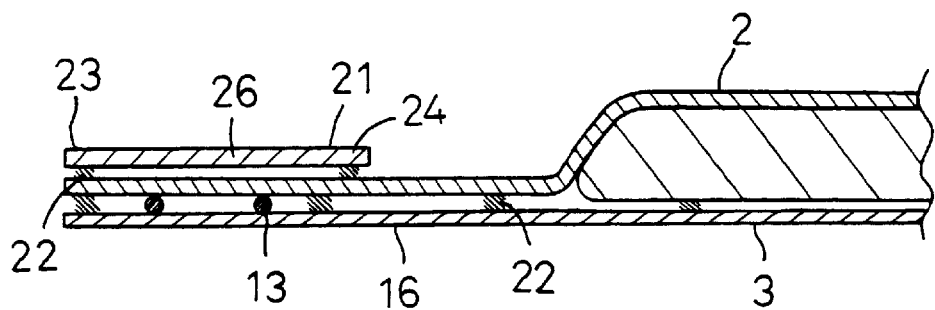
FIG. 3 is a sectional view taken along line III—III in FIG. 2.

FIG. 3 is a sectional view taken along line III—III in FIG. 2. Along the upper end 16 of the front waist region 6, the topsheet 2 and the backsheet 3 are joined together by means of hot melt adhesive 22. The slippage-resistant sheet 21 is attached in the vicinity of its upper zone 23 (left-hand zone as viewed in FIG. 3) as well as its lower zone 24 (right-hand zone as viewed in FIG. 3) to the upper surface of the topsheet 2 by means of hot melt adhesive 22. An intermediate zone 26 of the slippage-resistant sheet 21 defined between the upper and lower zones 23, 24 may be either attached or not attached to the topsheet 2, the latter case is illustrated in FIG. 3. The adhesive 22 is applied on the slippage-resistant sheet 21 so as to leave the respective outermost edges of the upper and lower zones 23, 24 free and therefore there is no possibility that the adhesive 22 might come in contact with the wearer's skin. The slippage-resistant sheet 21 may be formed by various materials, for example, a nonwoven fabric made of elastic fiber based on rubber such as urethane rubber, a nonwoven fabric made of the elastic fiber of 30~100% by weight and inelastic synthetic fiber of 70~0% by weight, a sheet based on rubber such as urethane rubber and a foamed sheet made of foamed urethane or the like. The foamed sheet is preferably of open cell type to improve a breathability of the diaper 1.

The diaper 1 constructed as has been described above can be easily put on by pulling the diaper 1 upward with the upper end 16 of the front waist region 6 held with the finger tips without the finger slipping off from the upper end 16. The slippage-resistant sheet 21 having its intermediate zone 26 not attached to the topsheet 2 as in the case of the embodiment shown by FIG. 3 is particularly advantageous since the intermediate zone 26 is relatively movable together with the wearer's finger tips and effective to improves a slippage-resistant effect. Additionally, the effect of the slippage-resistant sheet 21 can be improved by adjusting a friction coefficient presented by respective peripheral edges 27 (See FIGS. 1 and 2) of the leg-openings 12 on their inner surfaces to be lower than the friction coefficient presented by the slippage-resistant sheet 21. For example, a static friction coefficient of the former may be adjusted to be ⅓ or less of the static friction coefficient of the latter and a dynamic friction coefficient of the former may be adjusted to be ½ or less of the dynamic coefficient of the latter to improve the effect of the slippage-resistant sheet 21 correspondingly. In this case, the inner surfaces of said peripheral edges 27 may be defined by a spun lace nonwoven fabric or a spun bond nonwoven fabric made of conjugated fiber comprising polypropyrene as a core and polyethylene as a sheath wherein said conjugated fiber may be in crimped state or not. It is also possible to reduce the friction coefficient of the inner surfaces of the peripheral edges 27 by appropriately surface-treating them.

Figure 4:
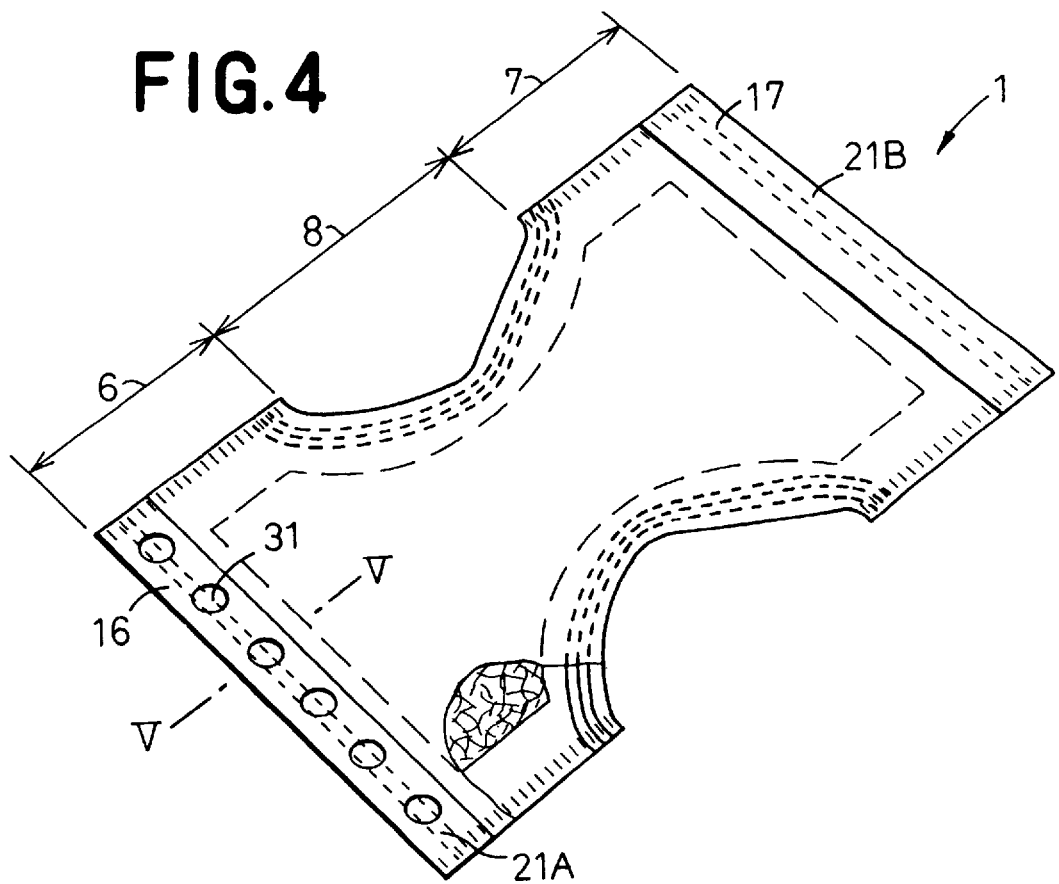
FIG. 4 is a view similar to FIG. 2 but showing another embodiment of this invention.

FIG. 4 is a view similar to FIG. 2 but showing another embodiment of this invention. According to this embodiment of the diaper 1, the inner surfaces of the upper ends 16, 17 of the front and rear waist regions 6, 7, respectively, are formed by a front slippage-resistant sheet 21A and a rear slippage-resistant sheet 21B both made of foamed urethane, respectively. The front slippage-resistant sheet 21A is formed with a plurality of through-holes 31 arranged intermittently in the circumferential direction.

Figure 5:
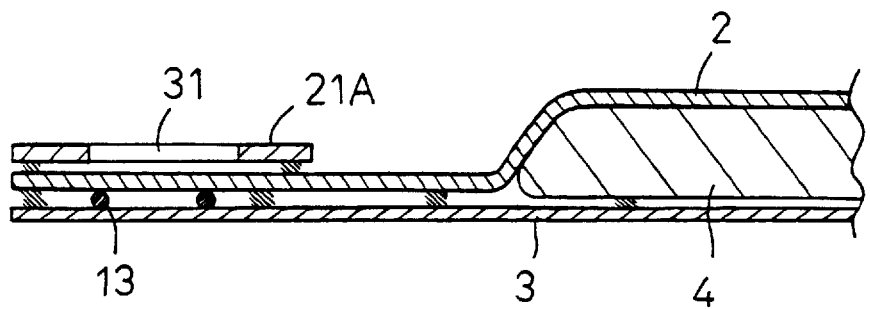
FIG. 5 is a sectional view taken along line V—V in FIG. 4.

FIG. 5 is a sectional view taken along line A—A in FIG. 4. The through-hole 31 of the front slippage-resistant sheet 21A has a diameter of at least 5 mm and extends through the sheet 21A in the direction of its thickness.

As will be apparent from FIGS. 4 and 5, this diaper 1 may be provided with the slippage-resistant sheets 21 (21A, 21B) in both the front and rear waist regions 6, 7. The through-holes 31 as those of the front slippage-resistant sheet 21A are effective to prevent the finger tips once engaged with these through-holes 31 as the diaper 1 is held with the finger tips from slipping off from the diaper 1.

Figure 6:
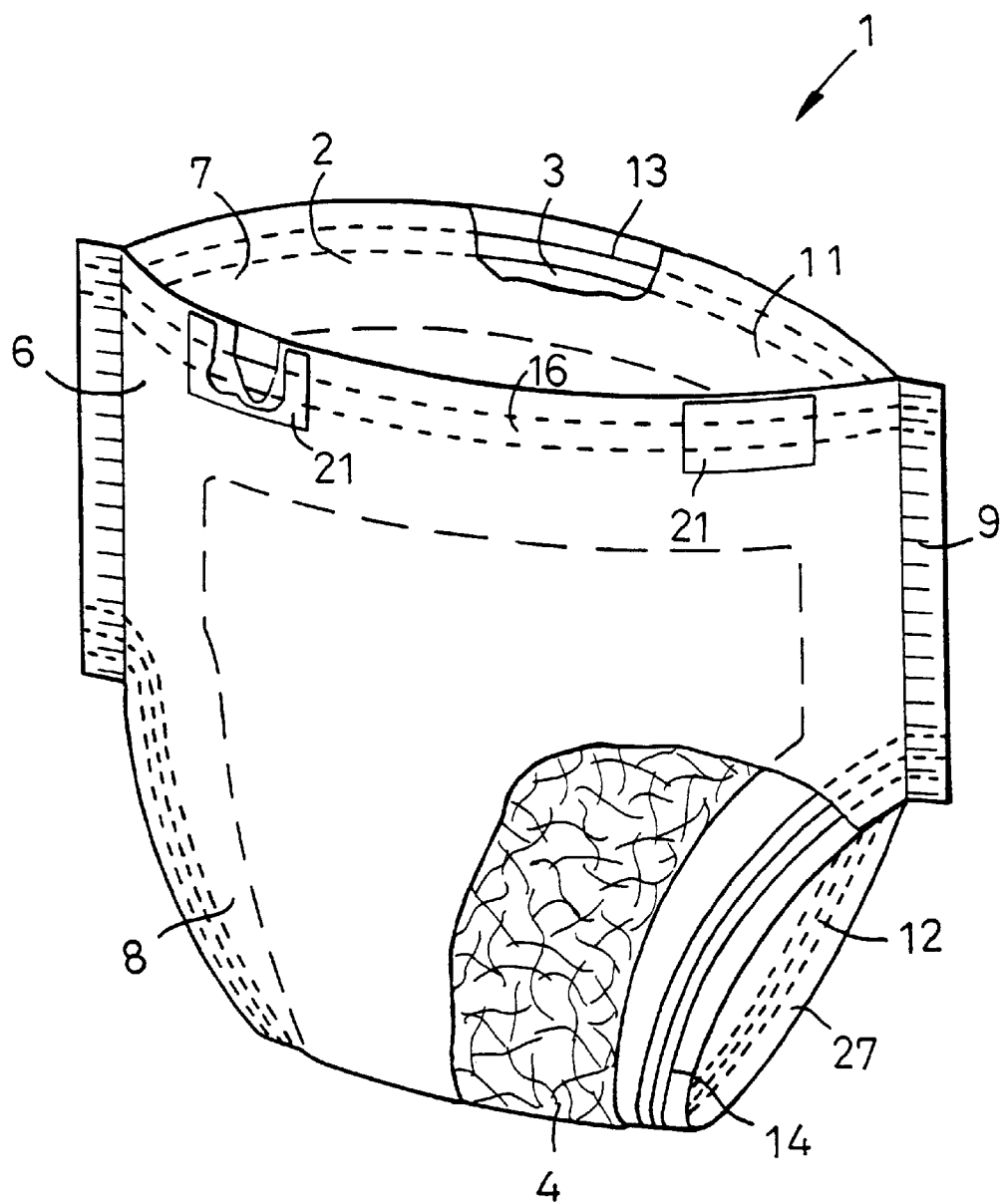
FIG. 6 is a view similar to FIG. 1 but showing still another embodiment of this invention.

FIG. 6 is a view similar to FIG. 1 but showing still another embodiment of this invention. According to this embodiment, the outer surface of the front waist region 6 is provided along the upper end 16 defining the waist-opening 11 with a pair of the slippage sheets 21 spaced from each other in the circumferential direction. In this case, these slippage sheets 21 have a static friction coefficient and/or a dynamic friction coefficient higher than those presented by the inner surface of the zone other than said longitudinal end 16. In such diaper 1, it is also possible to attach an additional slippage-resistant sheet 21 to the inner surface of the front waist region 6 along its upper end 16. It is also possible to attach the slippage-resistant sheets 21 to the outer surface and/or the inner surface of the rear waist region 7 along its upper end 17 in addition to or in the place of those attached to the front waist region 6. The slippage-resistant sheets 21 arranged intermittently in the circumferential direction are not limited to one pair as in the embodiment shown in FIG. 6 but it is also possible to provide a single slippage-resistant sheet 21 or three or more slippage-resistant sheets 21 in the circumferential direction.

To exploit this invention, the stock materials conventionally used in the relevant art may be used to form the topsheet 2 and the backsheet 3 and the absorbent core 4, respectively. This invention is applicable not only to the diaper 1 as shown and described, but also to disposable pants, disposable training pants or the like.

What is claimed is:

1. A disposable pull-on garment having an elasticized waist-opening and a pair of elasticized leg-openings, the garment further comprising:

a front waist region;

a rear waist region;

a crotch region;

the front and rear waist regions, each having inner and outer surfaces which include inner and outer peripheral edge surfaces of the waist opening and inner and outer surfaces of remaining zones; and wherein at least one of the inner and outer peripheral edge surfaces of the waist-opening is provided with a slippage-resistant sheet having a friction coefficient higher than a friction coefficient of the inner surfaces of the remaining zones, and wherein said slippage-resistant sheet is formed with a plurality of through-holes arranged intermittently in the circumferential direction and each of said through-hole has a diameter of 5 mm or larger.

2. The garment according to claim 1, wherein said slippage-resistant sheet has a width of 60 mm or less as measured vertically of said garment.

3. The garment according to claim 1, wherein said slippage-resistant sheet has a static friction coefficient of 0.8 or higher.

4. The garment according to claim 1, wherein said slippage-resistant sheet has a static friction coefficient of 0.8 or higher and a dynamic friction coefficient of 0.035 or higher.

5. The garment according to claim 4, wherein said static coefficient of friction presented by said slippage-resistant sheet is at least three times greater than a static coefficient of friction presented by an inner surface of a peripheral edge of each of said elasticized leg openings and said dynamic friction coefficient is at least two times greater than a dynamic friction coefficient presented by the inner surface of the peripheral edge of each of said elasticized leg openings.

6. The garment according to claim 1, wherein said slippage-resistant sheet extends circumferentially of said garment and has upper and lower zones attached to said garment while intermediate zones defined between said upper and lower zones are not attached to said garment.

7. The garment according to claim 1, wherein said slippage-resistant sheet contains polyurethane.

8. The garment according to claim 1, wherein said garment comprises a liquid-pervious topsheet, a liquid-impervious backsheet and an absorbent core disposed between these two sheets.

9. The garment according to claim 1, wherein said slippage-resistant sheet is attached onto at least one of the inner and outer peripheral edge surfaces of the waist-opening by an adhesive wherein the adhesive is applied on an inner surface of the slippage-resistant sheet so as to leave respective outermost edges of upper and lower zones of the slippage-resistant sheet free of adhesive.

* * * * *